United States Patent
Birkhold et al.

(10) Patent No.: US 12,232,901 B2
(45) Date of Patent: Feb. 25, 2025

(54) X-RAY IMAGING METHOD, X-RAY IMAGING SYSTEM, AND COMPUTER PROGRAM PRODUCT

(71) Applicant: Siemens Healthineers AG, Forchheim (DE)

(72) Inventors: Annette Birkhold, Stuttgart (DE); Markus Kowarschik, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/772,167

(22) Filed: Jul. 13, 2024

(65) Prior Publication Data

US 2025/0017541 A1    Jan. 16, 2025

(30) Foreign Application Priority Data

Jul. 13, 2023 (DE) ...................... 10 2023 206 656.4

(51) Int. Cl.
*A61B 6/00* (2024.01)
*A61B 6/50* (2024.01)

(52) U.S. Cl.
CPC .............. *A61B 6/481* (2013.01); *A61B 6/504* (2013.01); *A61B 6/5223* (2013.01)

(58) Field of Classification Search
None
See application file for complete search history.

(56) References Cited

U.S. PATENT DOCUMENTS

| | | | |
|---|---|---|---|
| 6,397,097 | B1 | 5/2002 | Requardt |
| 6,597,938 | B2 | 7/2003 | Liu |
| 7,974,682 | B2 | 7/2011 | Gonzalez |

(Continued)

FOREIGN PATENT DOCUMENTS

| | | |
|---|---|---|
| DE | 102006040939 A1 | 3/2008 |
| DE | 102011078678 A1 | 1/2013 |
| DE | 102012200715 A1 | 7/2013 |

OTHER PUBLICATIONS

Decision to Grant Patent for German App. No. 10 2023 206 656.4 decision dated May 28, 2024, with English Translation.

(Continued)

*Primary Examiner* — Hoon K Song
(74) *Attorney, Agent, or Firm* — Lempia Summerfield Katz LLC (57) ABSTRACT

In an X-ray imaging method, a first time length that corresponds to a time length for a contrast agent to flow from a defined contrast-agent injection location to a defined proximal location of a hollow organ, and a second time length that corresponds to a time length for a contrast agent to flow from the proximal location to a defined distal location of the hollow organ are obtained. During a first acquisition phase, a first sequence of projection images is produced. Each projection image at least partially represents the hollow organ under a different respectively defined projection direction. The first acquisition phase begins the first time length after an injection start time for injecting the contrast agent, and a duration of the first acquisition phase equals the second time length. A time-resolved three-dimensional reconstruction of the hollow organ is produced based on the projection images in the first sequence.

15 Claims, 3 Drawing Sheets

(56) References Cited

U.S. PATENT DOCUMENTS

| | | |
|---|---|---|
| 8,538,506 B2 | 9/2013 | Niethammer |
| 2013/0188771 A1 | 7/2013 | Kyriakou |
| 2013/0237815 A1 | 9/2013 | Klingenbeck |
| 2015/0201894 A1* | 7/2015 | Baumgart .............. A61B 6/481 378/62 |
| 2021/0133960 A1* | 5/2021 | Vaz ........................ A61B 6/481 |
| 2022/0164953 A1* | 5/2022 | Gulsun ................. G06T 7/0012 |
| 2024/0169540 A1* | 5/2024 | Bouwman ............. G06T 7/0016 |
| 2024/0257350 A1* | 8/2024 | Kowarschik ......... A61B 6/5211 |

OTHER PUBLICATIONS

German Office Action for German App. No. 10 2023 206 656.4 mailed Apr. 9, 2024, with English Translation.

Ruedinger, K. L., et al. "4D-DSA: development and current neurovascular applications." American Journal of Neuroradiology 42.2 (2021): 214-220.

\* cited by examiner

X-RAY IMAGING METHOD, X-RAY IMAGING SYSTEM, AND COMPUTER PROGRAM PRODUCT

This application claims the benefit of German Patent Application No. DE 10 2023 206 656.4, filed on Jul. 13, 2023, which is hereby incorporated by reference in its entirety.

BACKGROUND

The present embodiments relate to an X-ray imaging method for time-dependent three-dimensional representation of at least one hollow organ of a person, an X-ray imaging system for time-dependent three-dimensional representation of at least one hollow organ of a person, and a corresponding computer program product.

In order to produce a three-dimensional reconstruction of an organ to be depicted by X-ray imaging, a number of X-ray projection images are acquired at different projection directions, for example, and the three-dimensional reconstruction is obtained by backprojection of the respective projection images. For example, it is also possible to produce in this way three-dimensional reconstructions of hollow organs, such as vascular systems, for example. The term three-dimensional angiography is used in this case.

In addition, it is possible to produce X-ray projection images before administering a contrast agent and to produce X-ray projection images after or during administration of the contrast agent. It is also possible to subtract from each other X-ray projection images under the same projection direction, in which the contrast agent is and is not depicted, so that the hollow organs and, if applicable, instruments, may be better discerned in the resultant subtraction images. These subtraction images may likewise form the basis of a three-dimensional reconstruction. The term used in this case is three-dimensional digital subtraction angiography (3D-DSA). There are also approaches in which the subtraction is not performed until in the three-dimensions.

If projection images are acquired while the contrast agent is propagating in the hollow organ, time-resolved three-dimensional reconstructions may be produced. This allows a contrast agent bolus to be monitored at different points in time and from different viewing angles. If this is combined with the subtraction technique, the technology is termed 4D-DSA. In the publication by K. L. Ruedinger et al., "4D-DSA: Development and Current Neurovascular Applications," American Journal of Neuroradiology, 42(2) 214-220, 2021, the authors describe the development, acquisition, reconstruction, and current applications of 4D-DSA.

In order to produce a time-resolved 3D reconstruction, also referred to as a 4D reconstruction or time-resolved three-dimensional representation or 4D representation, of one or more hollow organs of a person in the described manner, it is typical to produce first a conventional three-dimensional reconstruction from the two-dimensional reconstruction images produced during administration of the contrast agent. For this purpose, for example, it is necessary to have available, from a sufficient number of projection directions, projection images that each contain the hollow organ entirely filled by contrast agent. The two-dimensional reconstruction images, which provide the contrast agent flow in the at least one hollow organ in the form of hollow-organ segments that are partially filled by contrast agent, are integrated by reprojection into the previously generated three-dimensional reconstruction.

One challenge that arises here is to have available a sufficiently large number of two-dimensional projection images for creating the three-dimensional reconstruction that contain hollow organs entirely filled by contrast agent, and also to have available a time-resolved depiction of the contrast agent bolus in the entire region of interest. If this is not the case, then artifacts may arise, or there may be gaps in the time-resolved representation, in which, for example, the propagation of the contrast agent bolus in certain relevant regions of the hollow organ is not depicted.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the disadvantages in the X-ray imaging for time-resolved three-dimensional (3D) representation of at least one hollow organ of a person may be at least partially resolved.

The present embodiments are based on the idea of delaying an acquisition phase for producing a sequence of projection images that at least partially represent the at least one hollow organ from different projection directions, by a first time length after an injection start time for injecting the contrast agent. The first time length corresponds to a person-specific time length for the contrast agent to flow from a defined contrast-agent injection location to a defined proximal location of the at least one hollow organ, where the time length of the acquisition phase is equal to a second time length that corresponds to a person-specific time length for the contrast agent to flow from the proximal location to a defined distal location of the at least one hollow organ.

According to one aspect of the present embodiments, an X-ray imaging method is specified for time-resolved three-dimensional representation of at least one hollow organ of a person. In this method, a first time length is obtained (e.g., by at least one computing unit of an X-ray imaging system). The first time length corresponds to a person-specific time length for a contrast agent (e.g., a certain defined contrast agent) to flow from a defined contrast-agent injection location for the person to a defined proximal location of the at least one hollow organ. A second time length is obtained (e.g., by the at least one computing unit). The second time length corresponds to a person-specific time length for the contrast agent to flow from the proximal location to a defined distal location of the at least one hollow organ.

During a first acquisition phase, a first sequence of projection images is produced, where each projection image in the first sequence at least partially represents the at least one hollow organ under a different respectively defined projection direction. The first acquisition phase is started the first time length after an injection start time for injecting the contrast agent at the contrast-agent injection location (e.g., begins after an injection start time by the first time length), and a duration of the first acquisition phase is equal to the second time length (e.g., the first acquisition phase ends after the injection start time by the sum of the first time length and the second time length). A time-resolved three-dimensional (3D) reconstruction of the at least one hollow organ is produced (e.g., by the at least one computing unit) based on the projection images in the first sequence.

The first time length and the second time length may be obtained, for example, by the first time length and the second time length being stored on a storage medium of the at least one computing unit and being read out by the at least one computing unit. The at least one computing unit obtains, for example, also the injection start time (e.g., that point in time at which the injection of the contrast agent is started at the contrast-agent injection location). For example, for this purpose, an information signal may be produced by user input or automatically when the injection starts, and transferred to the at least one computing unit. The injection of the contrast agent itself is not part of the X-ray imaging method, however.

The first time length and the second time length are, for example, specific time lengths for precisely that person whose at least one hollow organ is meant to be represented by the X-ray imaging method. The first time length and the second time length may be determined according to the present embodiments before the X-ray imaging method, or, in some embodiments, may be determined also as part of the X-ray imaging method before the first acquisition phase.

The first acquisition phase being started the first time length after the injection start time may be understood to be, for example, that the acquisition of an initial projection image in the first sequence is started by the first time length around the injection start time. The duration of the first acquisition phase being equal to the second time length may be understood to be, for example, that a final projection image in the first sequence is produced the second time length after the start of the first acquisition phase. For example, tolerances are taken into account, for example, relating to the time period needed to produce a projection image, the time period needed to set up the particular projection direction, the time period needed for the data capture, and so on. The first sequence of projection images then consists, for example, of the initial projection image and the final projection image and of a multiplicity of further projection images acquired between the initial and final projection images.

The first sequence corresponds, for example, to a time sequence, or time-ordered sequence, of the projection images, where the total number of projection images in the first sequence is defined. Each projection image in the first sequence at least partially representing the at least one hollow organ under a different respectively defined projection direction may be understood, for example, to be that the individual projection directions are defined for all the projection images in the first sequence, and each differ from one another for all the projection images in the first sequence. The projection directions of two different projection images in the first sequence are therefore always different from each other.

The statements relating to the first sequence may be applied, if applicable, analogously to further sequences of projection images.

The contrast-agent injection location corresponds, for example, to a point in the vascular system (e.g., the blood vessel system) of the person at which the contrast agent is injected (e.g., into a venous blood vessel of the person). The projection images in the first sequence do not necessarily represent, and in general do not represent, the contrast-agent injection location. The first time length is therefore generally greater than zero and may lie in the region of a few tenths of seconds to a number of (e.g., several) seconds.

For example, a defined region of interest, in which at least part of the at least one hollow organ lies, is represented by the first sequence of projection images. The contrast-agent injection location does not necessarily lie in the region of interest, and generally lies outside the region of interest. The proximal location may be understood to be the location at which the contrast agent bolus first reaches the region of interest after the injection at the contrast-agent injection location. In this sense, the proximal location may therefore be understood to be the location closest to the contrast-agent injection location. The distal location may accordingly correspond to the location inside the region of interest that the contrast agent bolus reaches last, or at which the contrast agent bolus leaves the region of interest. In this sense, the distal location may therefore be understood to be the location farthest from the contrast-agent injection location.

The time-resolved three-dimensional reconstruction of the at least one hollow organ being produced based on the projection images in the first sequence may be understood to be, for example, that at least the projection images in the first sequence are used to produce the time-resolved three-dimensional reconstruction. For example, further projection images that were not produced during the first acquisition phase but, for example, after the first acquisition phase are also used for this purpose. Since the first acquisition phase begins at time T1, where it is assumed that the contrast-agent injection time equals zero and T1 denotes the first time length, and ends at time T1+T2, where T2 denotes the second time length, the first acquisition phase covers the entire relevant time period during which the contrast agent bolus moves from the proximal location to the distal location.

In a second acquisition phase that follows the first acquisition phase, it is possible to produce, for example, further projection images that depict the at least one hollow organ while the at least one hollow organ is full of the contrast agent in the entire region of interest. The projection images from the second acquisition phase may then likewise be used to produce the time-resolved three-dimensional reconstruction.

For example, the projection images from the second acquisition phase may be used to produce a static three-dimensional reconstruction of the at least one hollow organ, and the projection images in the first sequence from the first acquisition phase may be backprojected into this static three-dimensional reconstruction in order to realize the time resolution.

As mentioned above, the process of contract agent injection itself is generally not part of the X-ray imaging method according to the present embodiments. It should still be pointed out, however, that the contrast agent injection, as is also the case in known methods for time-resolved three-dimensional representation, takes place over a time period that allows a sufficient number of projection images in which the at least one hollow organ is completely full of contrast agent in the region of interest. For example, the contrast agent may be administered over the entire first acquisition phase, and, if applicable, over the entire second acquisition phase.

The method may also be implemented in some embodiments as a 4D-DSA method. In this case, the projection images in the first sequence, and, if applicable, the projection images from the second acquisition phase and in the corresponding second sequence of projection images correspond to object images, vascular images, or fill images. The additional mask images required for the DSA, which represent the at least one hollow organ without the contrast agent, are then produced, for example, before the first acquisition time period, or later, when the contrast agent is no longer in the at least one hollow organ.

The time length for the contrast agent to flow from the contrast-agent injection location to the proximal location may vary according to the blood flow rate or anatomical conditions of the actual person. The same applies to the time length for the contrast agent to flow from the proximal location to the distal location. Obtaining or determining, according to the present embodiments, the first time length and the second time length in a person-specific manner for the actual person, and controlling, according to the present embodiments, the first acquisition phase such that the first acquisition phase begins at the time T1 and ends at the time T1+T2, prevent the undesirable situation in which projection images from certain projection directions are acquired before the contrast agent bolus has even reached the region of interest, and in which the first acquisition phase ends before the contrast agent bolus has reached the distal location and hence the time-resolved information is incomplete.

This achieves that the time-resolved three-dimensional reconstruction may represent in full the time-resolved flow of the contrast agent bolus in the entire region of interest from the proximal location to the distal location. This would not be possible reliably, for example, if start and end times of the first acquisition phase were to be set based on assumed delay times or empirical values or the like.

According to at least one embodiment, a preparatory sequence of projection images is produced during a preparatory phase before the injection start time, with each projection image in the preparatory sequence representing the proximal location and the distal location. The preparatory sequence is started at the same time as a further injection start time for injecting the contrast agent at the contrast-agent injection location. The first time length and the second time length are determined based on the projection images in the preparatory sequence.

At the further injection start time, which accordingly lies before the injection start time, the contrast agent is injected in advance for the purpose of determining the first time length and the second time length. A contrast-agent test bolus may thus be observed in order to determine the first time length and the second time length. At the injection start time, for example, there is no longer any contrast agent from the preparatory phase in the at least one hollow organ.

The projection images in the preparatory sequence need not necessarily be acquired from different projection directions. It is possible, however, that the projection images in the preparatory sequence are acquired from two or more different projection directions, and hence, that the preparatory sequence contains two or more different subsequences, each having a constant projection direction. The first time length and the second time length may be determined more reliably in this manner (e.g., if the proximal location and the distal location are not in the same plane). Even then, however, it is not necessary for the number of different projection directions during the preparatory sequence to be similar or equal to the number of different projection directions during the first acquisition phase. For example, it is not necessary for the projection images in the preparatory sequence to be suitable for a three-dimensional reconstruction. The number of projection images from the preparatory phase may be less than (e.g., significantly less than) the number of projection images during the first acquisition phase. Alternatively or additionally, the X-ray intensity and/or a frame rate may also be lower during the preparatory sequence than for producing the first sequence during the first acquisition phase. This reduces the exposure of the person to radiation in the preparatory phase.

Since the projection images in the preparatory sequence are produced in a time-defined manner, each projection image in the preparatory sequence may be assigned to a point in time after the time of injection. It may thus be discerned when the contrast-agent test bolus reaches the proximal location and the distal location, and consequently, the first time length and the second time length may be determined.

Known intensity thresholding methods relating to the image intensity in the projection images in the preparatory sequence may be used to determine the first time length and/or the second time length during the preparatory sequence based on the projection images in the preparatory sequence. Hence, for example, a defined region around the proximal location may be analyzed in order to determine that projection image in the preparatory sequence in which the image intensity in the region around the proximal location is greater than or equal to a defined threshold value for the first time. The time at which the projection image identified in this manner is acquired then corresponds, for example, to the first time length.

In addition, for example, a defined region around the distal location may be analyzed in order to determine that projection image in the preparatory sequence in which the image intensity in the region around the distal location is greater than or equal to the threshold value or a further defined threshold value for the first time. The time at which the projection image identified in this manner is acquired then corresponds, for example, to the sum of the first time length and the second time length.

It is also possible to use other image analysis algorithms (e.g., algorithms trained based on machine learning) in order to identify the corresponding projection image in which the contrast-agent test bolus reaches the proximal location and the distal location respectively for the first time. For example, it is also hence possible that a user does not have to select the proximal location or the distal location specifically in the relevant X-ray projection image. Instead, for example, a characteristic vessel structure or a characteristic point in the vessel structure of the at least one hollow organ may be designated by the user, and a suitably trained algorithm may be applied to the projection images in the preparatory sequence in order to identify automatically the associated projection images that correspond to the first time length and the second time length, respectively.

The proximal location and the distal location may vary, for example, depending on the actual application and/or depending on the hollow organ actually to be depicted or represented. For example, the proximal location may correspond to a bifurcation of the internal carotid artery or the like. The distal location may, for example, correspond to a point on the sigmoid sinus, or a point at a defined distance from a venous malformation, an aneurysm, or an arteriovenous fistula, and so on.

According to at least one embodiment, each projection image in the preparatory sequence represents the proximal location and the distal location under the same defined projection direction. Alternatively, the preparatory sequence consists of two or more subsequences, each containing two or more projection images, where each projection image in the preparatory sequence represents the proximal location and the distal location, and the respective projection directions within each subsequence are the same, and differ from each other for different subsequences.

A simple and quick preparatory sequence may be implemented in this way, in which T1 and T2 may nonetheless be determined reliably.

In different embodiments, it is also possible to produce, in a known manner, based on the projection images in the preparatory sequence, respective subtraction images, and then to determine the first time length and the second time length accordingly based on these subtraction images.

According to at least one embodiment, a first preparatory sequence of projection images is produced during a preparatory phase before the injection start time, with each projection image in the first preparatory sequence representing the proximal location. A second preparatory sequence of projection images is produced during the preparatory phase, with each projection image in the second preparatory sequence representing the distal location. The first preparatory sequence is started at the same time as a first further injection start time for injecting the contrast agent at the contrast-agent injection location. The second preparatory sequence is started at the same time as the first further injection start time or at the same time as a second further injection start time for injecting the contrast agent at the contrast-agent injection location. The first time length is determined based on the projection images in the first preparatory sequence, and the second time length is determined based on the projection images in the second preparatory sequence.

For example, the projection images in the first preparatory sequence do not represent the distal location, and the projection images in the second preparatory sequence do not represent the proximal location. In other words, the first time length and the second time length are ascertained based on different preparatory sequences. This allows the respective time lengths to be determined more precisely by establishing more precisely the proximal and distal locations (e.g., if these lie spatially relatively far apart from each other).

For example, the projection direction may be constant for all the projection images in the first preparatory sequence, and the projection direction may likewise be constant for the projection images in the second preparatory sequence. The projection direction in the first preparatory sequence may be the same as the projection direction in the second preparatory sequence, or may be different therefrom. It is also possible that the first preparatory sequence and/or the second preparatory sequence has two or more subsequences that differ in terms of their respective projection directions, which are constant within the subsequences.

According to at least one embodiment, the X-ray imaging method is a method for 4D-DSA.

According to at least one embodiment, during a first mask acquisition phase, a first mask sequence of projection images is produced, where each projection image in the first mask sequence at least partially represents the at least one hollow organ under a different projection direction in each case. Each projection image in the first mask sequence is associated with exactly one projection image in the first sequence, so that the projection direction of the projection image in the first mask sequence is the same as the projection direction of the associated projection image in the first sequence. For each projection image in the first mask sequence, a first subtraction image is produced (e.g., by the at least one computing unit) by subtracting the projection image in the first mask sequence from the associated projection image in the first sequence. The time-resolved three-dimensional reconstruction is produced based on the first subtraction images (e.g., all of the produced first subtraction images).

The projection images in the first mask sequence are acquired here, for example, while the contrast agent is not yet present, or is no longer present, in the at least one hollow organ. Thus, such embodiments involve, for example, an X-ray imaging method for 4D-DSA. It is also implicit from the association of each of the projection images in the first mask sequence with exactly one projection image in the first sequence that the number of projection images in the first mask sequence is equal to the number of projection images in the first sequence.

The time length of the first mask acquisition phase may equal the time length of the first acquisition phase, but this is not necessarily the case. The subtraction of each projection image in the first mask sequence from the associated projection image in the first sequence may be performed in accordance with known DSA methods, and, for example, may also include preprocessing and processing acts for the respective projection images before the actual subtraction and/or postprocessing acts on the resultant subtraction image.

The time-resolved representation of the at least one hollow organ may thereby be displayed in greater detail and more accurately, and, according to the present embodiments, in full and reliably.

According to at least one embodiment, during a second acquisition phase, a second sequence of projection images is produced, where each projection image in the second sequence at least partially represents the at least one hollow organ under a different respectively defined projection direction. The second acquisition phase is started at the end time of the first acquisition phase (e.g., begins when the first acquisition phase ends). The time-resolved three-dimensional reconstruction is produced based on the projection images in the first sequence and based on the projection images in the second sequence.

In corresponding embodiments, the time-resolved three-dimensional reconstruction is produced, for example, based on the first subtraction images and corresponding second subtraction images that are produced based on the projection images in the second sequence.

The duration of the second acquisition phase is generally dependent on the X-ray imaging system used, the frame rate, the required image quality, and so on. The duration of the second acquisition phase is selected, for example, such that it is possible to acquire all the projection images that are required to produce the static three-dimensional reconstruction.

The projection directions of the individual projection images in the second sequence differ from each other, as was explained also with regard to the projection images in the first sequence. In addition, the projection directions of the projection images in the second sequence may also differ from all the projection directions of the projection images in the first sequence. The latter is not necessarily the case, however. For example, the projection directions of individual projection images, or even all the projection images, in the second sequence may match respective projection directions of projection images in the first sequence.

As already intimated above, the injection duration from the time of injection onwards may cover both the duration of the first acquisition phase and the duration of the second acquisition phase. For example, the injection duration may equal the sum of the durations of the first acquisition phase and the second acquisition phase. In such embodiments, for example, the static three-dimensional reconstruction of the at least one hollow organ may be produced based on the projection images in the second sequence, if applicable based on corresponding second subtraction images. The projection images in the first sequence, or the first subtraction images, may each be reprojected, and the resultant reprojections may each be inserted into the static three-dimensional reconstruction.

It is thereby possible to produce a sequence of three-dimensional reconstructions, where a single reconstruction in the sequence corresponds to a combination of the static three-dimensional reconstruction with a reprojection of a corresponding projection image in the first sequence or of the corresponding first subtraction image. The sequence of three-dimensional reconstructions may then be interpreted as a time-resolved three-dimensional reconstruction, or four-dimensional reconstruction, of the at least one hollow organ.

According to at least one embodiment, a stop signal for automatically terminating a contrast agent injection of the contrast agent is produced at a point in time that lies in the first time length before an end time of the second acquisition phase. For example, the contrast agent injection is terminated automatically based on the stop signal.

The stop signal may be transferred, for example, to a contrast agent pump for injecting the contrast agent, and the contrast agent pump may terminate the contrast agent injection according to the stop signal.

In such embodiments, the injection duration covers the duration of the first acquisition phase but does not entirely cover the duration of the second acquisition phase. For example, the injection duration equals the sum of the durations of the first acquisition phase and the second acquisition phase minus the first time length. This exploits the fact that even after the contrast injection has terminated, the at least one hollow organ in the entire region of interest is still full of contrast agent for the first time length. The static three-dimensional reconstruction may consequently also be produced in that way. This therefore saves on contrast agent and thereby reduces the physical stress on the patient.

According to at least one embodiment, during a second mask acquisition phase, a second mask sequence of projection images is produced, where each projection image in the second mask sequence at least partially represents the at least one hollow organ under a different projection direction in each case. Each projection image in the second mask sequence is associated with exactly one projection image in the second sequence, so that the projection direction of the projection image in the second mask sequence is the same as the projection direction of the associated projection image in the second sequence. For each projection image in the second mask sequence (e.g., by the at least one computing unit), a second subtraction image is produced by subtracting the projection image in the second mask sequence from the associated projection image in the second sequence. The time-resolved three-dimensional reconstruction is produced based on the second subtraction images and based on the first subtraction images.

The statements and explanations relating to the first mask sequence may be applied analogously also to the second mask sequence.

According to at least one embodiment, the projection directions of the projection images in the first sequence and in the second sequence are characterized by respective angles within a defined (e.g., contiguous) angle range in a defined plane. During the first acquisition phase for acquiring the first sequence, a first subrange (e.g., a contiguous subrange) of the angle range is traversed, and during the second acquisition phase for acquiring the second sequence, a second subrange (e.g., a contiguous subrange) of the angle range is traversed. The second subrange is adjacent to the first subrange.

In other words, the second subrange, for example, follows the first subrange and does not overlap the first subrange.

The angle that characterizes the respective projection directions may be given by, for example, an angle that is included by a line connecting the X-ray source to the X-ray detector and lying, for example, perpendicular to a detector surface of the X-ray detector, and a defined reference direction within the plane. The X-ray source and the X-ray detector are arranged and mounted such that the X-ray source and the X-ray detector may be rotated about a common rotational axis that is perpendicular to the aforementioned plane. This may be realized, for example, by arranging the X-ray source and the X-ray detector on a C-arm. Each projection direction may thereby be defined by a corresponding angle from 0° to 360°.

Only rotation about one rotational axis is considered here. In suitable X-ray imaging systems, however, it may also be possible that the X-ray source and the X-ray detector may be rotated in different planes. This results in corresponding developments of the X-ray imaging method according to the present embodiments.

Without loss of generality, it may be assumed, for example, that the projection direction of the initial projection image in the first sequence corresponds to an angle of 0°. The angle range may then be described by $[0°, \alpha_{max}]$ where $\alpha_{max}<360°$. The first subrange is then given by $[0°, \alpha_1]$, and the second subrange is given by $[\alpha_1, \alpha_2]$, where $0°<\alpha_1<\alpha_2<\alpha_{max}$.

Within the first subrange, the angles of the projection images in the first sequence are, for example, evenly distributed or approximately evenly distributed. Within the second subrange, the angles of the projection images in the second sequence are, for example, evenly distributed or approximately evenly distributed.

For example, the first subrange and the second subrange are traversed immediately in succession and, for example, in the same direction.

This allows both the first acquisition phase and the second acquisition phase to be realized by just one angular traverse of the angle range.

According to at least one embodiment, the projection directions of the projection images in the first mask sequence and in the second mask sequence are characterized by respective angles within the angle range. During the first mask acquisition phase for acquiring the first mask sequence, the first subrange is traversed, and during the second mask acquisition phase for acquiring the second mask sequence, the second subrange is traversed.

In this case, the first subrange and the second subrange may likewise be traversed in the same direction.

This allows both the first mask sequence and the second mask sequence to be captured also by one single angular traverse of the entire angle range.

According to at least one embodiment, during the first acquisition phase for acquiring the first sequence, the entire angle range is traversed (e.g., in full), and during the second acquisition phase for acquiring the second sequence, the angle range is traversed (e.g., is traversed again), for example, in full.

As a result, the total angle range may be smaller than in the previously mentioned embodiments, in which the two subranges of the angle range are traversed in the same direction in order to capture the first sequence and the second sequence of projection images.

For example, in the embodiments mentioned in which the angle range is traversed in full both during the first acquisition phase and during the second acquisition phase, the angle range may be traversed in a first direction during the first acquisition phase, and in a second direction that is opposite to the first direction during the second acquisition phase. A time delay between the first acquisition phase and the second acquisition phase may thereby be reduced.

According to at least one embodiment in which the angle range is traversed in full both during the first acquisition phase and during the second acquisition phase, a duration of the second acquisition phase equals the second time length.

It is thereby possible to use the same speed of rotation or frame rate in producing the second acquisition sequence as in producing the first acquisition sequence. In alternative embodiments, however, it is also possible to use a time length for the second acquisition phase that differs from the second time length. In this case, the respective requirements for producing the static three-dimensional reconstruction and the time-resolved information may be taken into account independently of each other.

According to at least one embodiment in which the angle range is traversed in full both during the first acquisition phase and during the second acquisition phase, the first mask sequence is produced during the first mask acquisition phase, and the second mask sequence is produced during the second mask acquisition phase. According to at least one such embodiment, during the first mask acquisition phase for acquiring the first mask sequence, the angle range is traversed (e.g., is traversed in full), and during the second mask acquisition phase for acquiring the second mask sequence, the angle range is traversed (e.g., is traversed again), for example, in full.

According to at least one embodiment, during the first mask acquisition phase, the angle range is traversed in the first direction, and during the second mask acquisition phase, is traversed in the second direction, or vice versa.

According to at least one embodiment, a duration of the first mask acquisition phase and/or a duration of the second mask acquisition phase equals the second time length. Thus, for example, the durations of the first mask acquisition phase, the second mask acquisition phase, the first acquisition phase, and the second acquisition phase may each equal the second time length.

According to at least one embodiment, the projection directions of the projection images in the first sequence are characterized by respective angles within a defined angle range in a defined plane. The angle range is traversed during the first acquisition phase, where a parameter for producing the projection images in the first sequence is adjusted according to the second time length and the angle range (e.g., a size of the angle range).

In other words, the parameter is determined according to the second time length and according to the angle range, and the projection images in the first sequence are produced in accordance with the parameter determined in this manner.

For example, the parameter may be a single-image rate, also known as the frame rate, the number of projection images in the first sequence, an X-ray dose per projection image, and so on. The parameter may be calculated, for example, based on one or more of the variables. In setting the parameter, it may be provided, for example, that a corresponding three-dimensional reconstruction for the angle range may be facilitated in sufficient quality.

According to a further aspect of the present embodiments, an X-ray imaging system is specified for time-resolved three-dimensional representation of at least one hollow organ of a person. The X-ray imaging system has an X-ray source, an X-ray detector, and a drive mechanism for positioning the X-ray source and the X-ray detector with respect to an acquisition region according to different projection directions. The X-ray imaging system has at least one computing unit that is configured to obtain (e.g., to read from a storage medium) a first time length. The first time length corresponds to a person-specific time length for a contrast agent to flow from a defined contrast-agent injection location for the person to a defined proximal location of the at least one hollow organ. The at least one computing unit is configured to obtain (e.g., to read from the storage medium) a second time length that corresponds to a person-specific time length for the contrast agent to flow from the proximal location to a defined distal location of the at least one hollow organ.

The at least one computing unit is configured to control the drive mechanism, the X-ray source, and the X-ray detector to produce, during a first acquisition phase, a first sequence of projection images, where each projection image in the first sequence at least partially represents the at least one hollow organ under a different respectively defined projection direction. The first acquisition phase begins the first time length after an injection start time for injecting the contrast agent at the contrast-agent injection location, and a duration of the first acquisition phase equals the second time length. The at least one computing unit is configured to produce, based on the projection images in the first sequence, a time-resolved three-dimensional reconstruction of the at least one hollow organ.

A computing unit may be understood to be, for example, a data processing unit that contains a processing circuit. For example, the computing unit may thus process data for performing computing operations. These also include operations for performing indexed accesses to a data structure (e.g., to a look-up table (LUT)).

The computing unit may contain, for example, one or more computers, one or more microcontrollers, and/or one or more integrated circuits (e.g., one or more application-specific integrated circuits (ASIC), one or more field-programmable gate arrays (FPGA), and/or one or more systems on a chip (SoC)). The computing unit may also contain one or more processors (e.g., one or more microprocessors, one or more central processing units (CPU), one or more graphics processing units (GPU), and/or one or more signal processors, such as one or more digital signal processors (DSP)). The computing unit may also contain a physical or virtual interconnection of computers or others of the aforementioned units.

In various example embodiments, the computing unit contains one or more hardware and/or software interfaces and/or one or more memory units.

A memory unit may be configured as a volatile data storage medium (e.g., as a dynamic random access memory (DRAM) or a static random access memory (SRAM)) or as a non-volatile data storage medium (e.g., as a read-only memory (ROM), as a programmable read-only memory (PROM), as an erasable programmable read-only memory (EPROM), as an electrically erasable programmable read-only memory (EEPROM), as a flash memory or flash EEPROM, as a ferroelectric random access memory (FRAM), as a magnetoresistive random access memory (MRAM), or as a phase-change random access memory (PCRAM)).

The X-ray source and the X-ray detector are, for example, always positioned and/or aligned identically relative to each other regardless of the given projection direction at the time. For example, the X-ray source and the X-ray detector may be rigidly connected to each other (e.g., via a C-arm or the like). The drive mechanism contains, for example, one or more motors or gearing mechanisms for moving the source and the detector (e.g., simultaneously) in order to set up the individual projection directions.

Further embodiments of the X-ray imaging system follow directly from the various embodiments of the X-ray imaging method according to the present embodiments, and vice versa. For example, individual features and associated explanations and advantages relating to the various embodiments for the X-ray imaging method may be applied analogously to corresponding embodiments of the X-ray imaging system. For example, the X-ray imaging system according to the present embodiments is configured or programmed to perform an X-ray imaging method according to the present embodiments. For example, the X-ray imaging system according to the present embodiments performs the X-ray imaging method according to the present embodiments.

According to a further aspect of the present embodiments, a computer program containing commands is specified. When the commands are executed by an X-ray imaging system according to the present embodiments (e.g., by the at least one computing unit of the X-ray imaging system), the commands cause the X-ray imaging system to perform an X-ray imaging method according to the present embodiments.

For example, the commands may exist as program code. The program code may be provided, for example, as binary code or assembler and/or as source code of a programming language (e.g., C) and/or as program script (e.g., Python).

According to a further aspect of the present embodiments, a computer-readable storage medium (e.g., a non-transitory computer-readable storage medium) that stores a computer program is specified.

The computer program and the computer-readable storage medium according to the present embodiments may each be regarded as a computer program product containing the commands.

The claims, the figures, and the description of the figures contain further features of the invention.

The features and feature combinations mentioned above in the description, and the features and feature combinations mentioned below in the description of the figures and/or shown in the figures may be included by the invention not just in the particular combination stated but also in other combinations. For example, the invention may include embodiments and feature combinations that do not have all the features of a claim in the original wording. Further, the invention may include embodiments and feature combinations that go beyond or differ from the feature combinations presented in the dependency references of the claims.

The invention is described in greater detail below with reference to specific exemplary embodiments and associated schematic drawings. In the figures, identical or functionally equivalent elements may be denoted by the same reference signs. The description of identical or functionally equivalent elements is not necessarily repeated when referring to different figures.

DETAILED DESCRIPTION

Figure 1:
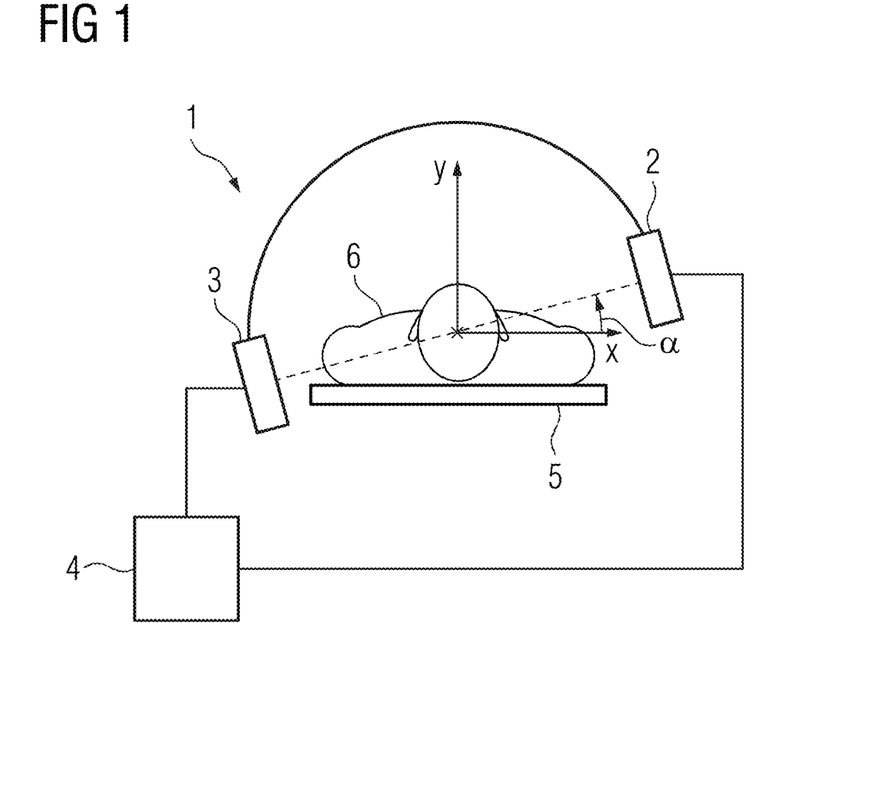
FIG. 1 shows a schematic representation of an example embodiment of an X-ray imaging system.
Figure 3:
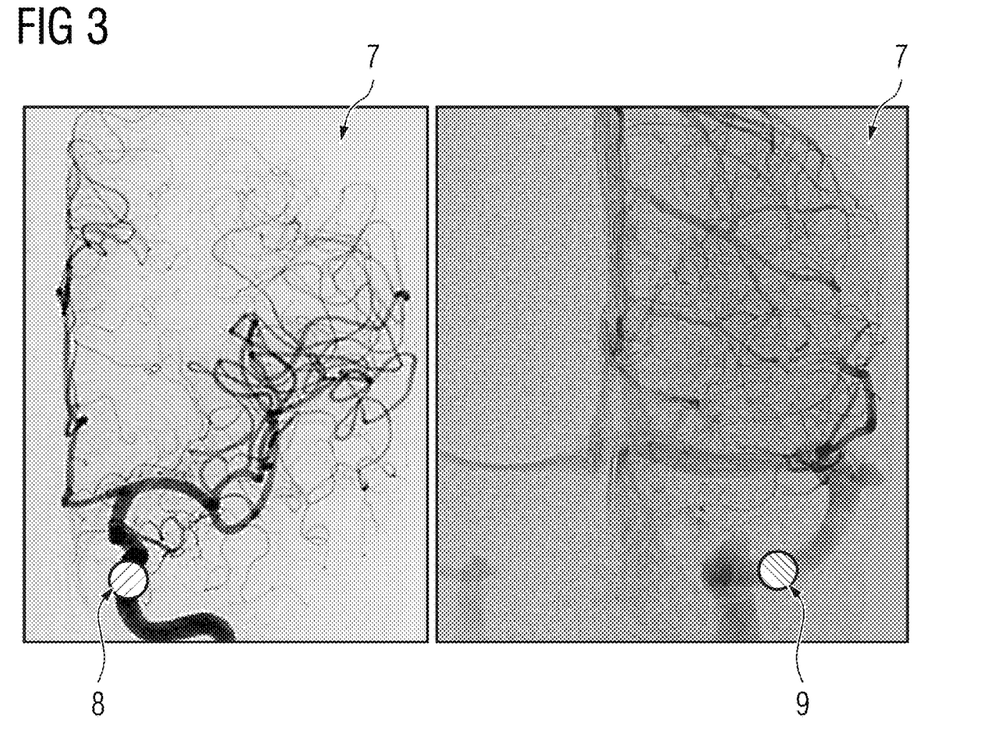
FIG. 3 shows schematic representations of at least one hollow organ of a person, and of a proximal location and a distal location.

FIG. 1 shows schematically an example embodiment of an X-ray imaging system 1 for time-resolved three-dimensional (3D) representation of at least one hollow organ 7 (see FIG. 3) of a person 6. The X-ray imaging system 1 has an X-ray source 2 and an X-ray detector 3, and a drive mechanism for positioning the X-ray source 2 and the X-ray detector 3 with respect to an acquisition region for positioning the person 6, or the at least one hollow organ 7, according to different projection directions. For example, the acquisition region may correspond to a region on a patient couch 5 or the like, which may be acquired by the X-ray source 2 and the X-ray detector 3.

A projection direction may be specified, for example, by an angle α, for example, that is included by a connecting line between the X-ray source 2 and the X-ray detector 3 and an x-axis of a coordinate system spanning a plane in which, using the drive mechanism, the X-ray source 2 and the X-ray detector 3 may rotate about a rotational axis that is, for example, parallel to a z-axis that is perpendicular to the x-axis and y-axis.

In addition, the X-ray imaging system 1 has at least one computing unit 4 that may control the X-ray source 2 to emit X-ray radiation, and may obtain relevant detector data from the X-ray detector 3. The relevant detector data corresponds to a projection image according to the instantaneous projection direction. The at least one computing unit 4 may also control the drive mechanism in order to set up the various projection directions.

Figure 2:
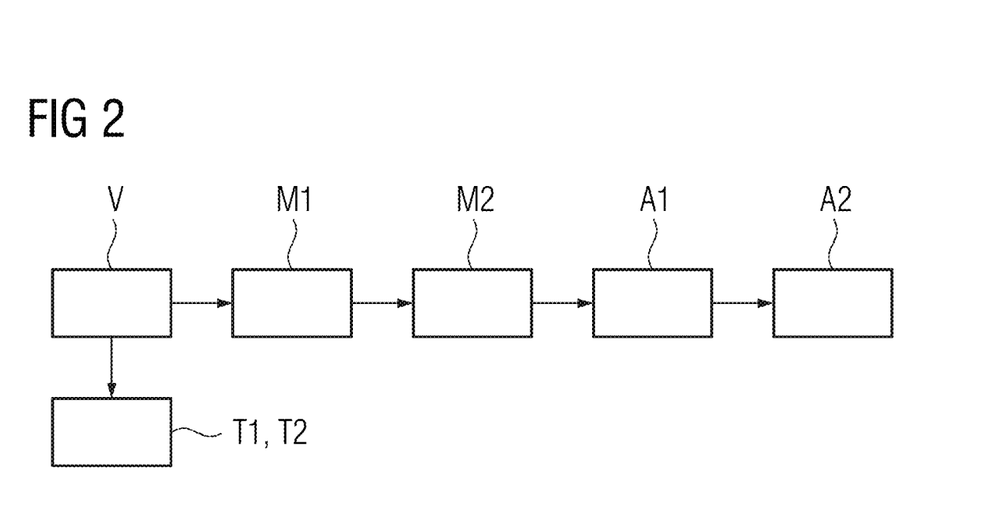
FIG. 2 shows a schematic flow diagram of an example embodiment of an X-ray imaging method.

The X-ray imaging system 1 may be used to perform an X-ray imaging method according to the present embodiments. FIG. 2 shows a schematic flow diagram of an example embodiment of such an X-ray imaging method.

During a preparatory phase V, a first time length T1 and a second time length T2 are determined for the person 6. The first time length T1, for example, corresponds to a person-specific time length for a contrast agent to flow from a defined contrast-agent injection location for the person 6 to a defined proximal location 8 (see FIG. 3) of the at least one hollow organ 7. The second time length T2 corresponds to a person-specific time length for the contrast agent to flow from the proximal location 8 to a defined distal location 9 (see FIG. 3) of the at least one hollow organ 7. Two X-ray acquisitions (e.g., subtraction images) of a vascular tree during a venous phase and an arterial phase, respectively, after contrast agent administration are shown schematically in FIG. 3, and an example of a proximal location 8 in an example of a distal location 9 is marked. The vascular tree corresponds to the at least one hollow organ 7 in a suitable embodiment of the X-ray imaging method.

During a first acquisition phase A1, a first sequence of projection images is produced, where each projection image in the first sequence at least partially represents the at least one hollow organ 7 under a different respectively defined projection direction. The first acquisition phase A1, for example, begins the first time length T1 after the injection start time, at which the injection of the contrast agent is started at the contrast-agent injection location. A duration of the first acquisition phase is equal to the second time length T2.

For example, during a second acquisition phase A2 after the first acquisition phase A1, a second sequence of projection images may be produced, where each projection image in the second sequence at least partially represents the at least one hollow organ 7 under a different respectively defined projection direction. The second acquisition phase A2 begins at the time the first acquisition phase A1 ends.

A time-resolved three-dimensional reconstruction of the at least one hollow organ 7 is produced by the at least one computing unit 4 based on the projection images in the first sequence and, if applicable, based on the projection images in the second sequence. For example, a static three-dimensional reconstruction of the at least one hollow organ 7 may be produced based on the projection images in the second sequence, and the projection images in the first sequence may each be reprojected into the static three-dimensional reconstruction in order to produce overall the time-resolved three-dimensional reconstruction.

In some embodiments, the X-ray imaging method may be configured as a 4D-DSA method, for example. In this case, during a first mask acquisition phase M1, a first mask sequence of projection images is produced, where each projection image in the first mask sequence at least partially represents the at least one hollow organ 7 under a different projection direction in each case. Each projection image in the first mask sequence is associated with exactly one projection image in the first sequence, so that the projection direction of the projection image in the first mask sequence is the same as the projection direction of the associated projection image in the first sequence. For each projection image in the first mask sequence, a first subtraction image is produced by subtracting the projection image in the first mask sequence from the associated projection image in the first sequence.

For example, during a second mask acquisition phase M2, a second mask sequence of projection images is produced, where each projection image in the second mask sequence at least partially represents the at least one hollow organ 7 under a different projection direction in each case. Each projection image in the second mask sequence is associated with exactly one projection image in the second sequence, so that the projection direction of the projection image in the second mask sequence is the same as the projection direction of the associated projection image in the second sequence. For each projection image in the second mask sequence, a second subtraction image is produced by subtracting the projection image in the second mask sequence from the associated projection image in the second sequence.

The time-resolved three-dimensional reconstruction is then produced based on the first subtraction images and, for example, based on the second subtraction images. For example, the static three-dimensional reconstruction of the at least one hollow organ 7 may be produced based on the second subtraction images, and the first subtraction images may each be backprojected into the static three-dimensional reconstruction in order to produce the time-resolved three-dimensional reconstruction.

A preparatory sequence of projection images may be produced during the preparatory phase V, with each projection image in the preparatory sequence representing the proximal location 8 and the distal location 9. The preparatory sequence begins at the same time as a further injection start time for injecting the contrast agent at the contrast-agent injection location, and the first time length T1 and the second time length T2 are determined based on the projection images in the preparatory sequence.

Figure 4:
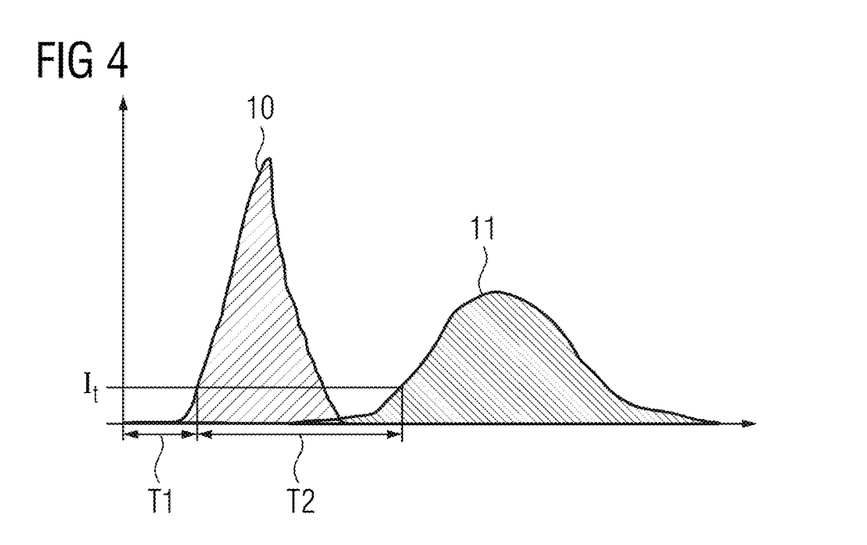
FIG. 4 shows schematically an image intensity curve at a proximal location and a distal location of at least one hollow organ.

FIG. 4 shows in this regard a time curve 10 of the image intensity of the projection images in the preparatory sequence at the proximal location 8, and a corresponding time curve 11 of the image intensity at the distal location 9.

The first time length T1 and the second time length T2 may be determined, for example, by determining points of intersection of the respective rising edges of the time curves 10, 11 with a horizontal line given by a defined threshold intensity $I_t$. The first time length T1 then corresponds to a point in time at which the time curve 10 at the proximal location 8 first reaches the threshold intensity $I_t$. The second time length T2 corresponds to the time period between the point of intersection of the curve 10 with the threshold intensity $I_t$ and the point in time at which the time curve 11 first exceeds the threshold intensity $I_t$. In other embodiments, different threshold intensities may also be used for the two time curves 10, 11. It is also not absolutely necessary for T1 and T2 to be determined based on the same preparatory sequence. For example, two different preparatory sequences may be used for T1 and T2.

The respective number of projection images during the first and second acquisition phases A1, A2, and hence the angular increments between directly successive projection images in the first acquisition phase A1, and, given a set duration, in the second acquisition phase A2, result, for example, from the desired image quality.

Figure 5:
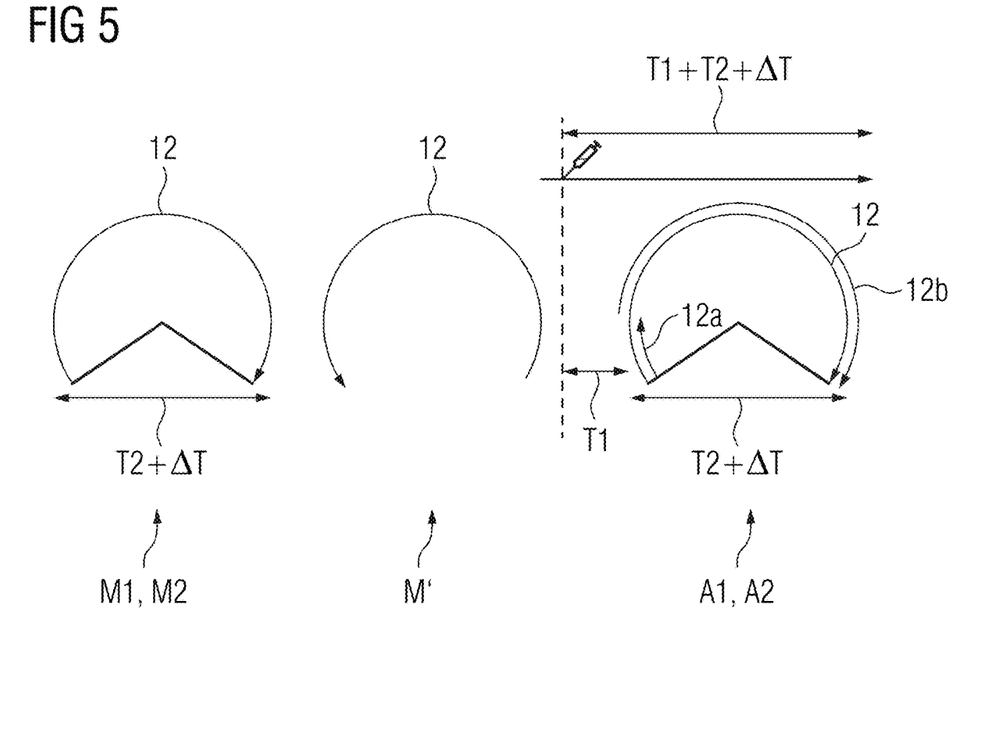
FIG. 5 shows a schematic flow diagram of a further example embodiment of the X-ray imaging method.

FIG. 5 shows schematically a procedure of a further example embodiment of an X-ray imaging method.

After the injection start time, and after an X-ray delay corresponding to the first time length T1, a first subrange 12*a* of an angle range 12 of the angle α is traversed in the first acquisition phase A1. The first subrange 12*a* is traversed, for example, within the second time length T2. Then, a second subrange 12*b* of the angle range 12 is traversed in the second acquisition phase A2 within a further time length ΔT. The first subrange 12*a* and the second subrange 12*b* together amount to the angle range 12, and are traversed in succession in the same direction. Therefore, including the X-ray delay, a time T1+T2+ΔT, for example, is needed to produce the first sequence and the second sequence.

The second subrange 12*b* may correspond, for example, to an angle range of 200° in total, and the first subrange may equal an angle range of 60°, for example. The angle α thus sweeps a total angle of 260° in the angle range 12. Angle ranges that differ from this may be chosen. It has been found that a reliable static three-dimensional reconstruction is possible for an angle range of 200°. The additional 60° of the first subrange 12*a* is then available for capturing the time-resolved information.

If the X-ray imaging method is being performed as a 4D-DSA method, during the mask phases M1, M2, overall, the entire angle range 12 is likewise traversed, for example, but not necessarily, within the same total time T2+ΔT. For example, the first subrange 12*a* may be traversed during the first mask acquisition phase M1, and the second subrange 12*b* may be traversed thereafter during the second mask acquisition phase M2. In an optional act M' between the second mask acquisition phase M2 and the first acquisition phase A1, the angle α may be reset by suitable positioning of the X-ray source 2 and the X-ray detector 3.

Figure 6:
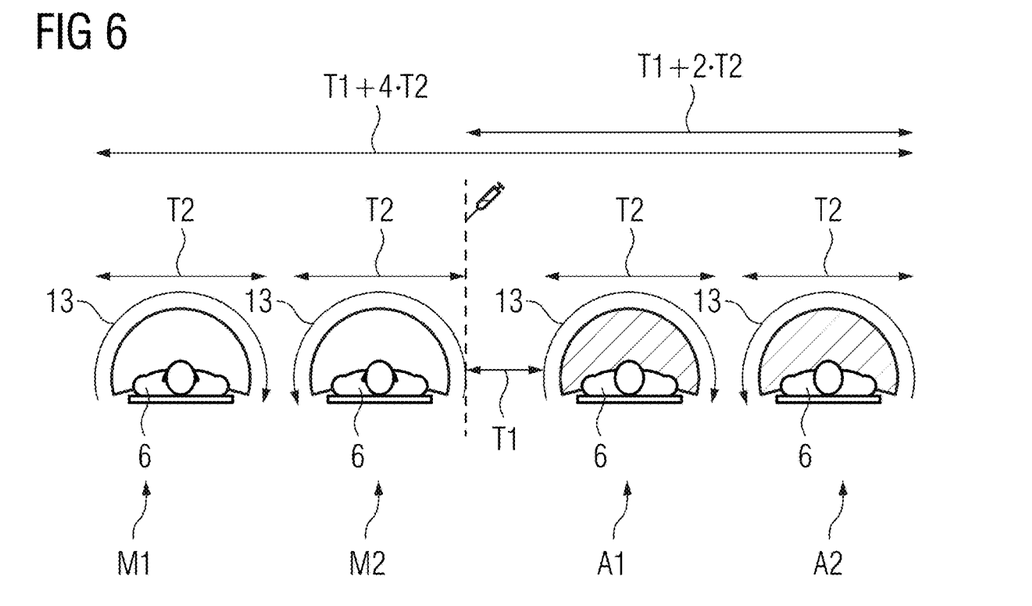
FIG. 6 shows a schematic flow diagram of a further example embodiment of an X-ray imaging method.

FIG. 6 shows a schematic procedure of a further example embodiment of an X-ray imaging method. Again in this case, the first acquisition phase A1 begins the first time length T1 after the time of injection. During the first acquisition phase A1, the angle α traverses within the second time length T2 an angle range 13 in a first direction. In the subsequent second acquisition phase A2, the angle α traverses the angle range 13 again (e.g., in a second direction) that is opposite to the first direction. This may likewise take place within the second time length T2, although this is not absolutely necessary.

Since the angle range 13 is traversed in full both during the first acquisition phase A1 and during the second acquisition phase A2, the angle range 13 may be chosen to be smaller than the angle range 12 in the example of FIG. 5. For example, the angle range 13 may equal 200°. If the second acquisition phase A2 also has a duration T2, then the time period from the time of injection until the completion of the second acquisition phase A2 equals T1+2*T2.

In the case of 4D-DSA, the angle range 13 may, for example, likewise be traversed twice in full before the injection start time: once in the first direction during the first mask acquisition phase M1; and in the second direction during the second mask acquisition phase M2. The mask acquisition phases M1, M2 may likewise each be equal to the second time length T2. In this case, the total acquisition time is given by T1+4*T2. Again, however, this is not absolutely necessary.

Independent of the grammatical term usage, individuals with male, female or other gender identities are included within the term.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An X-ray imaging method for time-resolved three-dimensional (3D) representation of at least one hollow organ of a person, the method comprising:
    obtaining a first time length that corresponds to a person-specific time length for a contrast agent to flow from a defined contrast-agent injection location for the person to a defined proximal location of the at least one hollow organ;
    obtaining a second time length that corresponds to a person-specific time length for the contrast agent to flow from the defined proximal location to a defined distal location of the at least one hollow organ;
    during a first acquisition phase, producing a first sequence of projection images, wherein each projection image in the first sequence at least partially represents the at least one hollow organ under a different respectively defined projection direction, wherein the first acquisition phase begins the first time length after an injection start time for injecting the contrast agent at the contrast-agent injection location, and a duration of the first acquisition phase equals the second time length; and
    producing a time-resolved 3D reconstruction of the at least one hollow organ based on the projection images in the first sequence.

2. The X-ray imaging method of claim 1, further comprising:
    producing a preparatory sequence of projection images during a preparatory phase before the injection start time, wherein each projection image in the preparatory sequence represents the proximal location and the distal location;
    starting the preparatory sequence at a same time as a further injection start time for injecting the contrast agent at the contrast-agent injection location; and
    determining the first time length and the second time length based on the projection images in the preparatory sequence.

3. The X-ray imaging method of claim 2, wherein:
    each projection image in the preparatory sequence represents the proximal location and the distal location under the same defined projection direction; or
    the preparatory sequence consists of two or more subsequences, each of the two or more subsequences containing two or more projection images, wherein each projection image in the preparatory sequence represents the proximal location and the distal location, and the respective projection directions within each subsequence of the two or more subsequences are the same, and differ from each other for different subsequences of the two or more subsequences.

4. The X-ray imaging method of claim 1, further comprising:
    producing a first preparatory sequence of projection images during a preparatory phase before the injection start time, wherein each projection image in the first preparatory sequence represents the proximal location;
    producing a second preparatory sequence of projection images during the preparatory phase, wherein each projection image in the second preparatory sequence represents the distal location;
    starting the first preparatory sequence at a same time as a first further injection start time for injecting the contrast agent at the contrast-agent injection location;
    starting the second preparatory sequence at a same time as the first further injection start time or at a same time as a second further injection start time for injecting the contrast agent at the contrast-agent injection location; and
    determining the first time length based on the projection images in the first preparatory sequence, and determining the second time length based on the projection images in the second preparatory sequence.

5. The X-ray imaging method of claim 1, further comprising:
    during a first mask acquisition phase, producing a first mask sequence of projection images, wherein each projection image in the first mask sequence at least partially represents the at least one hollow organ under a different projection direction in each case, wherein each projection image in the first mask sequence is associated with exactly one projection image in the first sequence, so that the projection direction of the projection image in the first mask sequence is the same as the projection direction of the associated projection image in the first sequence; and
    producing, for each projection image in the first mask sequence, a first subtraction image, the producing of the first subtraction image comprising subtracting the projection image in the first mask sequence from the associated projection image in the first sequence,
    wherein producing the time-resolved 3D reconstruction further comprises producing the time-resolved 3D reconstruction based on the first subtraction images.

6. The X-ray imaging method of claim 5, further comprising:
   during a second acquisition phase, producing a second sequence of projection images, wherein each projection image in the second sequence at least partially represents the at least one hollow organ under a different respectively defined projection direction, wherein the second acquisition phase begins at a time the first acquisition phase ends, and
   wherein producing the time-resolved 3D reconstruction further comprises producing the time-resolved 3D reconstruction based on the projection images in the second sequence.

7. The X-ray imaging method of claim 6, further comprising:
   during a second mask acquisition phase, producing a second mask sequence of projection images, wherein each projection image in the second mask sequence at least partially represents the at least one hollow organ under a different projection direction in each case, wherein each projection image in the second mask sequence is associated with exactly one projection image in the second sequence, so that the projection direction of the projection image in the second mask sequence is the same as the projection direction of the associated projection image in the second sequence; and
   producing, for each projection image in the second mask sequence, a second subtraction image, the producing of the second subtraction image comprising subtracting the projection image in the second mask sequence from the associated projection image in the second sequence, wherein producing the time-resolved 3D reconstruction further comprises producing the time-resolved 3D reconstruction based on the second subtraction images.

8. The X-ray imaging method of claim 7, wherein the projection directions of the projection images in the first sequence and in the second sequence are characterized by respective angles within a defined angle range in a defined plane, and
   wherein during the first acquisition phase, a first subrange of the angle range is traversed, and during the second acquisition phase, a second subrange of the angle range is traversed, the second subrange being adjacent to the first subrange.

9. The X-ray imaging method of claim 8, wherein the projection directions of the projection images in the first mask sequence and in the second mask sequence are characterized by respective angles within the angle range in the plane, and
   wherein the first subrange is traversed during the first acquisition mask phase, and the second subrange is traversed during the second mask acquisition phase.

10. The X-ray imaging method of claim 7, wherein the projection directions of the projection images in the first sequence are characterized by respective angles within a defined angle range in a defined plane, and
    wherein the angle range is traversed during the first acquisition phase, and the angle range is traversed during the second acquisition phase.

11. The X-ray imaging method of claim 10, wherein the angle range is traversed in a first direction during the first acquisition phase, and in a second direction that is opposite to the first direction during the second acquisition phase.

12. The X-ray imaging method of claim 10, wherein the projection directions of the projection images in the first mask sequence are characterized by respective angles within the angle range in the plane, and
    wherein the angle range is traversed during the first mask acquisition phase, and the angle range is traversed during the second mask acquisition phase.

13. The X-ray imaging method of claim 6, further comprising producing a stop signal for automatically terminating a contrast agent injection of the contrast agent at a point in time that lies within the first time length before an end time of the second acquisition phase.

14. The X-ray imaging method of claim 1, wherein the projection directions of the projection images in the first sequence are characterized by respective angles within a defined angle range in a defined plane,
    wherein the angle range is traversed during the first acquisition phase, and
    wherein a parameter for producing the projection images in the first sequence is adjusted according to the second time length (T2) and the angle range.

15. An X-ray imaging system for time-resolved three-dimensional (3D) representation of at least one hollow organ of a person, the X-ray imaging system comprising:
    an X-ray source;
    an X-ray detector;
    a drive mechanism for positioning the X-ray source and the X-ray detector with respect to an acquisition region according to different projection directions; and
    at least one computing unit that is configured to:
        obtain a first time length that corresponds to a person-specific time length for a contrast agent to flow from a defined contrast-agent injection location for the person to a defined proximal location of the at least one hollow organ;
        obtain a second time length that corresponds to a person-specific time length for the contrast agent to flow from the proximal location to a defined distal location of the at least one hollow organ;
        control the drive mechanism, the X-ray source, and the X-ray detector, such that, during a first acquisition phase, a first sequence of projection images is produced, wherein each projection image in the first sequence at least partially represents the at least one hollow organ under a different respectively defined projection direction, wherein the first acquisition phase begins the first time length after an injection start time for injecting the contrast agent at the contrast-agent injection location, and a duration of the first acquisition phase equals the second time length; and
        produce a time-resolved 3D reconstruction of the at least one hollow organ based on the projection images in the first sequence.

* * * * *